United States Patent [19]

Nakano et al.

[11] Patent Number: 5,066,817
[45] Date of Patent: Nov. 19, 1991

[54] DC115A COMPOUNDS PRODUCED BY STREPTOMYCES SP.

[75] Inventors: Hirofumi Nakano; Mitsunobu Hara, both of Machida; Tsuyoshi Mokudai, Hofu; Isao Kawamoto, Hiratsuka; Mayumi Yoshida, Sagamihara; Eiji Kobayashi, Shizuoka, all of Japan

[73] Assignee: Kyowa Hakko Kogyo Co., Ltd., Tokyo, Japan

[21] Appl. No.: 516,304

[22] Filed: Apr. 30, 1990

[30] Foreign Application Priority Data

May 8, 1989 [JP] Japan .................. 1-114783
Nov. 6, 1989 [JP] Japan .................. 1-288553

[51] Int. Cl.$^5$ .................. C07D 311/78; C07D 311/94
[52] U.S. Cl. .................. 549/384; 435/127; 435/253.5; 435/886; 514/453
[58] Field of Search .......... 435/886, 127, 253.5; 549/384; 514/453

[56] References Cited

FOREIGN PATENT DOCUMENTS

| 0339442 | 11/1989 | European Pat. Off. | ......... 435/127 |
| 0342363 | 11/1989 | European Pat. Off. | ......... 435/127 |
| 3031027 | 8/1986 | Japan | ......... 435/127 |
| 30115609 | 12/1986 | Japan | ......... 435/127 |

OTHER PUBLICATIONS

CRC Handbook of Antibiotic Compounds, CRC Press, U.S.A. (1981), pp. 61–69, 167–173, 315–317.

Primary Examiner—Lester L. Lee
Assistant Examiner—E. J. Kraus
Attorney, Agent, or Firm—Fitzpatrick, Cella, Harper & Scinto

[57] ABSTRACT

Disclosed are DC115A compounds represented by the following general formula:

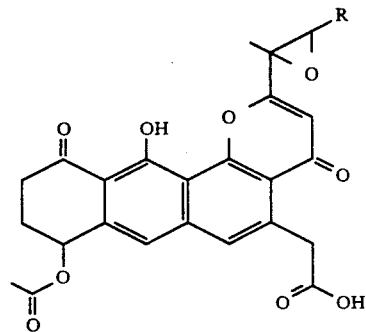

wherein R represents ethyl, propyl or 1-propenyl, and which have antibacterial and anti-tumor activity. DC115A compounds are produced by culturing a microorganism belonging to the genus Streptomyces.

5 Claims, No Drawings

DC115A COMPOUNDS PRODUCED BY STREPTOMYCES SP.

BACKGROUND OF THE INVENTION

The present invention relates to novel DC115A compounds.

DC115A compounds have antibacterial and antitumor activity and are useful as antibiotics and antitumor agents.

Many compounds such as anthracycline compounds, anthraquinone compounds and mitomycin compounds have been hitherto reported as anti-tumor antibiotics (CRC Handbook of Antibiotic Compounds, CRC Press, U.S.A., 1981).

However, compounds having the skeleton related to the present invention are unknown.

SUMMARY OF THE INVENTION

The present invention provides novel DC115A compounds having an excellent antibacterial and anti-tumor activity and which are represented by the following general formula:

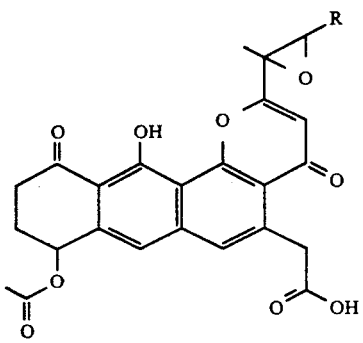

wherein R represents ethyl, propyl or 1-propenyl. DC115A compounds can be produced by culturing a DC115A compound-producing microorganism belonging to the genus Streptomyces in a medium.

DETAILED DESCRIPTION OF THE INVENTION

The present inventors have acquired a microorganism belonging to the genus Streptomyces from a soil sample obtained in Kanazawa City, Ishikawa Prefecture. It has been found that compounds obtained by culturing the strain are novel compounds having an excellent antibacterial and antitumor activity, and the present invention has been accomplished.

Of the DC115A compounds of the present invention, the compound wherein R is propyl is named DC115A1, the compound wherein R is ethyl is named DC115A2, and the compound wherein R is 1-propenyl is named DC115A3.

The physicochemical properties of the DC115A compounds are shown below.

DC115A1

(1) Molecular weight: 494
(2) Molecular formula: $C_{27}H_{26}O_9$
(3) Mass spectrum: SIMS: 495 $(M+1)^+$
   High resolution EIMS:
     Found: 450.1659 $(M^+ -44)$
     Calcd. for $C_{26}H_{26}O_7$: 450.1642
(4) Specific rotation: $[\alpha]_D^{25} = -217°$ (c=0.1, methanol)
(5) Ultraviolet absorption spectrum: (measured in methanol)
   $\lambda_{max}$ (nm): 216, 262, 375, 390
(6) Infrared absorption spectrum: (measured in KBr)
   $cm^{-1}$: 3440, 2960, 1740, 1650, 1618, 1425, 1365, 1230
(7) PMR spectrum: (measured in $CD_3OD$, 400 MHz, internal standard TMS)
   $\delta$(ppm) 7.51 (s, 1H), 7.33 (s, 1H), 6.32 (s, 1H), 6.15 (dd, J=7.0, 3.6 Hz, 1H), 4.26 (d, J=16.7 Hz, 1H), 4.17 (d, J=16.7 Hz, 1H), 3.24 (t, J=6.2 Hz, 1H), 3.02 (m, 1H), 2.82 (m, 1H), 2.39 (m, 1H), 2.32 (m, 1H), 2.17 (s, 3H), 1.84 (s, 3H), 1.50 (m, 4H), 0.86 (t, J=7.0 Hz, 3H)
(8) CMR spectrum: (measured in $CD_3OD$, 100 MHz, internal standard TMS)
   $\delta$(ppm) 205.6 (s), 180.4 (s), 175.6 (s), 171.9 (s), 166.8 (s), 165.5 (s), 158.8 (s), 141.9 (s), 141.9 (s), 138.4 (s), 129.6 (d), 121.0 (s), 118.1 (d), 114.6 (s), 112.9 (s), 111.9 (d), 70.5 (d), 67.6 (d), 60.9 (s), 42.8 (t), 35.3 (t), 30.7 (t), 28.7 (t), 21.1 (q), 20.3 (t), 20.2 (q), 14.0 (q)
(9) Solubility:
   Soluble in chloroform, dimethylsulfoxide, methanol, ethyl acetate and acetone; sparingly soluble in water and n-hexane.
(10) Color reaction:
   Positive in reaction with iodine
(11) Color and property of the compound:
   Yellow acidic substance
(12) Thin layer chromatography: silica gel thin layer (HPTLC plate Art. 15647, manufactured by Merck Inc.)
   The Rf value obtained by using toluene: acetone solution (1:1 v/v) as a developing solvent was 0.20.
   The Rf value obtained by using chloroform:methanol:acetic acid solution (20:1:0.1 v/v/v) as a developing solvent was 0.48.

DC115A2

(1) Molecular weight: 480
(2) Molecular formula: $C_{26}H_{24}O_9$
(3) Mass spectrum: SIMS: 481 $(M+1)^+$
(4) Specific rotation: $[\alpha]_D^{25} = -237°$ (c=0.1, methanol)
(5) Ultraviolet absorption spectrum: (measured in methanol)
   $\pi_{max}$ (nm): 216, 262, 375, 392
(6) Infrared absorption spectrum: (measured in KBr)
   $cm^{-1}$: 3420, 2970, 1720, 1650, 1615, 1420, 1360, 1230
(7) PMR spectrum: (Measured in $CD_3OD$, 400 MHz, internal standard TMS)
   $\delta$(ppm) 7.54 (s, 1H), 7.36 (s, 1H), 6.34 (s, 1H), 6.18 (dd, J=6.8, 3.6 Hz, 1H), 4.27 (d, J=16.6 Hz, 1H), 4.19 (d, J=16.6 Hz, 1H), 3.23 (t, J=6.4 Hz, 1H), 3.04 (m, 1H), 2.84 (m, 1H), 2.40 (m, 1H), 2.33 (m, 1H), 2.17 (s, 3H), 1.84 (s, 3H), 1.56 (m, 1H), 1.45 (m, 1H), 0.98 (t, J=7.5 Hz, 3H)
(8) CMR spectrum: (Measured in $CD_3OD$, 100 MHz, internal standard TMS)
   $\delta$(ppm) 205.7 (s), 180.5 (s), 175.8 (s), 172.1 (s), 166.9 (s), 165.6 (s), 158.9 (s), 141.9 (s), 141.9 (s), 138.5 (s), 129.7 (d), 121.0 (s), 118.2 (d), 114.7 (s), 113.0 (s), 111.9 (d), 70.6 (d), 68.7 (d), 61.1 (s), 42.9 (t), 35.3 (t), 28.7 (t), 22.3 (t), 21.1 (q), 20.2 (q), 10.3 (q)
(9) Solubility:
   Soluble in chloroform, dimethylsulfoxide, methanol, ethyl acetate and acetone; sparingly soluble in water and n-hexane.
(10) Color reaction:

Positive in reaction with iodine
(11) Color and property of the compound:
    Yellow acidic substance
(12) Thin layer chromatography: silica gel thin layer (HPTLC plate Art. 15647, manufactured by Merck Inc.)
    The Rf value obtained by using toluene:acetone soltuion (1:1 v/v) as a developing solvent was 0.16. The Rf value obtained by using chloroform:methanol:acetic acid solution (20:1:0.1 v/v/v) as a developing solvent was 0.48.

DC115A3

(1) Molecular weight: 492
(2) Molecular formula: $C_{27}H_{24}O_9$
(3) Mass spectrum: SIMS: 493 $(M+1)^+$
(4) Specific rotation: $[\alpha]_D^{25} = -349°$ (c=0.1, methanol)
(5) Ultraviolet absorption spectrum: (measured in methanol)
    $\lambda_{max}$ (nm): 216, 262, 375, 390
(6) Infrared absorption spectrum: (measured in KBr)
    $cm^{-1}$; 3460, 2950, 1742, 1650, 1620, 1426, 1370, 1230
(7) PMR spectrum: (measured in $CD_3OD$, 400 MHz, internal standard TMS)
    δ(ppm) 7.55 (s, 1H), 7.73 (s, 1H), 6.38 (s, 1H), 6.19 (dd, J=6.8, 3.5 Hz, 1H), 5.83 (m, 1H), 5.15 (m, 1H), 4.26 (d, J=16.7 Hz, 1H), 4.21 (d, J=16.7 Hz, 1H), 4.01 (d, J=7.9 Hz, 1H), 3.05 (m, 1H), 2.86 (m, 1H), 2.43 (m, 1H), 2.35 (m, 1H), 2.15 (s, 3H), 1.91 (s, 3H), 1.81 (dd, J=7.1, 1.8 Hz, 3H)
(8) CMR spectrum: (measured in $CD_3OD$, 100 MHz, internal standard TMS)
    δ(ppm) 205.7 (s), 180.6 (s), 175.5 (s), 172.0 (s), 166.7 (s), 165.5 (s), 158.9 (s), 141.9 (s), 141.9 (s), 138.2 (s), 134.8 (d), 129.7 (d), 124.1 (d), 120.9 (s), 118.1 (d), 114.7 (s), 113.0 (s), 111.5 (d), 70.5 (d), 62.9 (d), 61.1 (d), 42.7 (t), 35.3 (t), 28.7 (t), 21.1 (q), 19.8 (q), 13.7 (q)
(9) Solubility:
    Soluble in chloroform, dimethylsulfoxide, methanol, ethyl acetate and acetone; sparingly soluble in water and n-hexane.
(10) Color reaction:
    Positive in reaction with iodine
(11) Color and property of the compound:
    Yellow acidic substance
(12) Thin layer chromatography: silica gel thin layer (HPTLC plate Art. 15647, manufactured by Merck Inc.)
    The Rf value obtained by using toluene:acetone solution (1:1 v/v) as a developing solvent was 0.10. The Rf value obtained by using chloroform:methanol:acetic acid solution (20:1:0.1 v/v/v) as a developing solvent was 0.48.

The biological activities of DC115A1, DC115A2 and DC115A3 are described below.

(A) Antibacterial activity

The minimum inhibitory concentration (MIC) against various bacteria was determined by the agar dilution method (pH 7.0). The results are shown in Table 1.

TABLE 1

| Bacteria Tested | Minimum Inhibitory Concentration (μg/ml) | | |
|---|---|---|---|
| | DC115A1 | DC115A2 | DC115A3 |
| Staphylococcus aureus ATCC 6538P | 5.2 | 2.6 | 0.3 |
| Bacillus subtilis No. 10707 | 10 | 10 | 1.3 |
| Klebsiella pneumoniae ATCC 10031 | >100 | 10 | 5.2 |
| Salmonella typhi ATCC 9992 | >100 | >100 | 83 |
| Escherichia coli ATCC 26 | >100 | 83 | 21 |

(B) Growth inhibition against T24 cells

A T24 cell suspension ($2 \times 10^4$ cells/ml) prepared by suspending T24 cells in a medium comprising F10 medium (GIBCO Co., Ltd.), 0.1 g/ml fetal calf serum, 100 units/ml penicillin and 100 μg/ml streptomycin (hereinafter referred to as medium A) was put into wells of a 96-well microtiter plate in an amount of 0.1 ml per well. After incubation at 37° C. for 20 hours in a $C_2$-incubator, 0.05 ml of a sample appropriately diluted with medium A was added to each well. The cells were further cultured at 37° C. for 72 hours in the $CO_2$-incubator and the culture supernatant was removed. To the residue was added a medium comprising medium A and 0.02% Neutral Red in an amount of 0.1 ml per well, followed by culturing at 37° C. for one hour in the $CO_2$-incubator, whereby the cells were stained. After the culture supernatant was removed, the residue was washed once with physiological saline.

Then, the pigment was extracted with 0.001N hydrochloric acid/30% ethanol and absorbance at 550 nm was measured with a microplate reader. By comparing the absorbance of intact cells with those of the cells treated with a test compound at known concentrations, the concentration of the test compound at which the growth of the cells is inhibited by 50% ($IC_{50}$) was determined. The results are shown in Table 2.

Growth inhibition against $HeLaS_3$ cells $IC_{50}$ was determined in the same manner as in the case of T24 cells except that a suspension of $HeLaS_3$ cells ($3 \times 10^4$ cells/ml) prepared by suspending $HeLaS_3$ cell medium comprising MEM medium (Nissui Pharmaceutical Co., Ltd.) and 2 mM glutamine was used. The results are shown in Table 2.

TABLE 2

| Test Compound | $IC_{50}$ (μg/ml, 72 hours) | |
|---|---|---|
| | T24 | $HeLaS_3$ |
| DC115A1 | 0.17 | 0.22 |
| DC115A2 | 0.11 | 0.19 |
| DC115A3 | 0.14 | 0.42 |

From the results of (B) and (C) described above, it is evident that DC115A1, DC115A2 and DC115A3 inhibit the growth of tumor cells and are expected to be effective anti-tumor agents.

The process for producing the DC115A compounds is described below.

The DC115A compounds can be obtained by culturing in a medium a microorganism belonging to the genus Streptomyces and being capable of producing the DC115A compounds, allowing the DC115A compounds to accumulate in the culture, and recovering the DC115A compounds therefrom.

As the DC115A compound-producing strain, any strain may be used as long as it belongs to the genus Streptomyces and has the ability to produce the DC115A compound. Further, mutant strains derived from such strains by artificial mutation such as ultraviolet irradiation, X-ray irradiation and treatment with mutagens or by spontaneous mutation can also be used so long as they have the ability to produce the DC115A compounds. A typical strain is DO-115 strain.

The mycological characteristics of DO-115 strain are described below.

These characteristics of the strain were determined according to the procedures recommended by International Streptomyces Project (ISP) for characterization of species belonging to the genus Streptomyces [E. B. Shirling and D. Gottlieb: Int. J. Syst. Bacteriol., 16, 313-340 (1966)]. The isomer of diaminopimelic acid in the whole cell hydrolyzate was analyzed by the method of B. Becker, et. al. [Appl. Microbiol., 12, 421-423 (1964)]. Morphological study was made by using an optical microscope, and a scanning electron microscope was employed for observing the morphology of spore surface. The color indications are given according to the classification in the Color Harmony Manual (Container Corporation of America, 4th edition, 1958).

(1) Morphology

| | |
|---|---|
| Aerial mycelium | Branched |
| Substrate mycelium | Branched but not fragmented. |
| Spore | Long flexuous or loop-like chains of more than 10 arthrospores are formed on aerial mycelium. |
| Surface of spore | Spiny |
| Motility of spore | No motility is observed. |
| Shape and size of spore | oval (0.5 × 0.7 μm) |
| Formation of sclerotium and sporangium is not observed. | |

(2) Color

| | |
|---|---|
| Aerial mycelium | gray |
| Substrate mycelium | light brown or yellowish brown |
| Soluble pigment | light yellow |
| Melanin pigment | positive |

(3) Chemical composition of cell wall

Steric configuration of diaminopimelic acid: LL-form (4) Physiological properties Assimilation of carbon sources:

| | |
|---|---|
| Assimilable | glucose |
| Nonassimilable | xylose, inositol, mannitol, arabinose, rhamnose, raffinose, fructose, sucrose |
| Liquefaction of gelatin | negative |
| Hydrolysis of starch | positive |
| Coagulation of defatted milk | negative |
| Peptonization of defatted milk | positive |
| Decomposition of cellulose | positive |
| Growth temperature range | 16 to 37° C. (optimum: 28 to 32° C.) |

The actions upon gelatin, defatted milk and cellulose were observed after one month of culturing at 28° C., growth temperature range was determined after two days of culturing, and the other observations were made after two weeks of culutring at 28° C.

(5) Cultural characteristics on various agar media

DO-115 strain was cultured at 28° C. for 28 days on various agar media. The results are shown in Table 3.

TABLE 3

| Medium | Cultural Characteristics |
|---|---|
| Sucrose-nitrate agar medium | G: Poor |
| | AM: Poor, covert gray (2fe) |
| | SM: Colorless |
| | P: None |
| Glucose-asparagine agar medium | G: Moderate |
| | AM: Abundant, dark covert gray (2ih) |
| | SM: Golden brown to light brown (3pi-3lg) |
| | P: Light yellow |
| Glycerol-asparagine agar medium | G: Moderate |
| | AM: Poor, white |
| | SM: Bisque (3ec) |
| | P: None |
| Starch-agar medium | G: Moderate |
| | AM: Poor, white |
| | SM: Clove brown (3ni) |
| | P: Light yellow |
| Tyrosine agar medium | G: Poor |
| | AM: None |
| | SM: Camel (3ie) |
| | P: Light yellow |
| Nutrient agar medium | G: Moderate |
| | AM: Fair, griege (1fe) |
| | SM: Light brown (3lg) |
| | P: Light yellow |
| Yeast extract-malt extract agar medium | G: Poor |
| | AM: None |
| | SM: Light mustard tan (2ie) |
| | P: Light yellow |
| Oatmeal agar medium | G: Good |
| | AM: Poor, white |
| | SM: Clove brown (3pl) |
| | P: Brown |
| Peptone-yeast extract-ion agar medium | G: Poor |
| | AM: None |
| | SM: Colorless |
| | P: Brown |

Abbreviations are as follows. G: degree of growth, AM: formation of aerial mycelium and its color, SM: color of substrate mycelium, P: hue of soluble pigment.

DO-115 strain belongs to the Type I cell wall group according to the classification of actinomycetes by M. P. Lechevalier and H. A. Lechevalier [Int. J. Syst. Bacteriol., 20, 435-443 (1970)], since LL-diaminopimelic acid is contained in the whole cell hydrolyzate. On the basis of this characteristic and morphological characteristics, this strain should reasonably be designated as a strain of the genus Streptomyces.

For the identification of the species in this genus, a search was made through the Approved Lists of Bacterial Name of International Code of Nomenclature of Bacteria [V. B. D. Skerman, et al., Int. J. Syst. Bacteriol., 30, 225-420 (1980)], for a strain having taxonomical properties akin to those of DO-115 strain according to the descriptions of ISP [Int. J. Syst. Bacteriol., 18, 69-189 (1968), ibid., 18, 279-392 (1968), ibid., 19, 391-512 (1969), ibid., 22, 265-394 (1972), and R. E. Buchanan and N. E. Gibbons, Bergey's Manual of Determinative Bacteriology, 8th edition], based on the following characteristics of DO-115 strain: grayish aerial mycelium, flexuous or loop-like spore chains, spiny spore surface, the aforesaid assimilation patterns of carbon sources, and the ability to produce melanin-like pigment and light yellow soluble pigment.

As a result of the search, identification of the species having properties identical with those of DO-115 strain has turned out to be difficult. This strain has been deposited with the Fermentation Research Institute, Agency of Industrial Science and Technology, under the Budapest Treaty as Streptomyces sp. DO-115 with accession number FERM BP-2408 (date of the original deposit: May 1, 1989).

The method for culturing is described below.

For the culturing in the present invention, conventional methods for culturing actinomycetes are generally used. As the medium, either a synthetic medium or a natural medium can be employed so long as it contains proper amounts of assimilable carbon sources, nitrogen sources, inorganic substances, and substances required for the growth of the microorganism or acceleration of the production of the DC115A compounds.

As the carbon source, glucose, starch, dextrin, mannose, fructose, sucrose, lactose, xylose, arabinose, mannitol, molasses, etc. can be used alone or in combination. Further, hydrocarbons, alcohols, organic acids and the like can also be used depending on the assimilability of the strain.

As the nitrogen source, ammonium chloride, ammonium sulfate, ammonium nitrate, sodium nitrate, urea, peptone, meat extract, yeast extract, dry yeast, corn steep liquor, soybean powder, Casamino acid, etc. can be used alone or in combination.

If necessary, inorganic salts such as sodium chloride, potassium chloride, magnesium sulfate, calcium carbonate, potassium dihydrogenphosphate, dipotassium hydrogenphosphate, ferrous sulfate, calcium chloride, manganese sulfate, zinc sulfate and copper sulfate can also be added.

In addition, trace components capable of promoting the growth of the strain used or the production of the DC115A compounds can be appropriately added.

Culturing is usually carried out by liquid culture, and most preferably by submerged culture with stirring. Culturing temperature is 16° to 37° C., preferably 25° to 32° C. It is desirable to maintain the pH of the medium at 4 to 10, preferably 6 to 8, by adding aqueous ammonia, ammonium carbonate solution, etc. during the culturing.

Usually after one to seven days of liquid culture, the desired DC115A compounds are formed and accumulated in the culture broth and microbial cells.

Culturing is discontinued when the amount of the product in the culture reaches the maximum.

Isolation and purification of DC115A1, DC115A2 and DC115A3 from the culture are carried out by conventional methods for isolating and purifying microbial metabolites from culture. For example, the culture is separated into culture broth and microbial cells by filtration. The microbial cells are extracted with chloroform, acetone, etc. The extract is combined with the culture broth, and the mixture is passed through a column of an adsorbent of the polystyrene type, e.g., Diaion HP-20 (Mitsubishi Kasei Corporation) to adsorb the active component. Then, the active component is eluted with ethyl acetate, acetone, etc. The eluate is concentrated and subjected to silica gel column chromatography, high performance liquid chromatography, etc. to give DC115A1, DC115A2 and DC115A3 as light yellow powders.

During the culture and purification steps, DC115A1, DC115A2 and DC115A3 can be traced by bioassay using *Bacillus subtilis* No. 10707 or by thin layer chromatography using UV absorption as indication.

A certain embodiment of the present invention is illustrated by the following representative example.

EXAMPLE

Streptomyces sp. DO-115 was used as the seed strain. This strain was inoculated into 300 ml of a seed medium having the following composition in a 2-l Erlenmeyer flask, and subjected to shaking culture (rotation: 200 r.p.m.) at 30° C. for 48 hours.

Composition of the seed medium: 10 g/l peptone (Kyokuto Pharmaceutical Co., Ltd.), 1 g/l yeast extract, 5 g/l corn steep liquor, 20 g/l soluble starch, 10 g/l glucose, and 5 g/l calcium carbonate (pH 7.2 prior to sterilization).

The resulting seed culture was transferred into 15 l of a fermentation medium having the following composition in a 30-l jar fermenter in a ratio of 10% by volume. Culturing was carried out at 28° C. for 90 hours with aeration and stirring (rotation: 200 r.p.m., aeration: 15 l/min).

The pH of the medium was not controlled during the culturing.

Composition of the fermentation medium: 50 g/l soluble starch, 14 g/l dry yeast, 0.5 g/l $KH_2PO_4$, 0.5 g/l $MgSO_4.7H_2O$, 5 g/l calcium carbonate, 1.0 mg/l $CuSO_4$, 0.5 mg/l $NiSO_4.6H_2O$ and 1.0 mg/l $CrK(SO_4)_2.12H_2O$ (pH 7.0, adjusted with NaOH prior to sterilization).

After the culture broth was separated by filtration, 15 l of acetone was added to the cells. The mixture was shaken for extraction, and the precipitates were filtered off to give 14 l of an extract. The extract was concentrated to 3 l, which was then combined with 10 l of the culture broth. The mixture was passed through a column packed with 2 l of an adsorbent of the polystyrene type (Diaion HP-20) to adsorb the active substance.

After impurities were removed with deionized water and 30% methanol, the active substance was eluted with methanol. The obtained active fractions were concentrated and extracted with ethyl acetate. The extract was dehydrated over sodium sulfate, followed by concentration. The residue was passed through a silica gel column BW300 (Fuji Davison Chemical Co., Ltd.) and developed with toluene:acetone solution (5:1 v/v). The eluted fractions were taken in test tubes in 20 ml portions and the test tubes were numbered in the order of fractionation.

The eluate in each test tube was examined for the activity by using a silica gel thin layer (Art. 15647, manufactured by Merck Inc.). As a result, the active fraction containing DC115A1 (hereinafter referred to as Fraction 1) was found in test tube Nos. 50 to 65; the active fraction containing DC115A2 (hereinafter referred to as Fraction 2) was found in test tube Nos. 70 to 80; and the active fraction containing DC115A3 (hereinafter referred to as Fraction 3) was found in test tube Nos. 85 to 93.

Fraction 1 was concentrated, and the resulting yellowish green concentrate was passed through a silica gel column (Lichroprep Si60, manufactured by Merck Inc.) for adsorption, followed by development with chloroform:methanol:acetic acid solution (100:2:1 v/v/v) under a pressure of about 10 kg/cm². After the eluted active fractions were concentrated, the residue was again passed through the silica gel column and eluted with chloroform:methanol:acetic acid solution (100:2:1 v/v/v).

The obtained active fractions were concentrated and the residue was dissolved in methanol. The solution was applied to Sephadex LH20 column and elution was carried out with methanol. By concentrating the eluted active fractions, 12 mg of DC115A1 was obtained as yellow powder.

Fraction 2 and Fraction 3 were treated in a similar manner as above, whereby 8 mg of DC115A2 and 28 mg of DC115A3 were obtained from the respective fractions as yellow powders.

What is claimed is:

1. DC115A compounds represented by the following general formula:

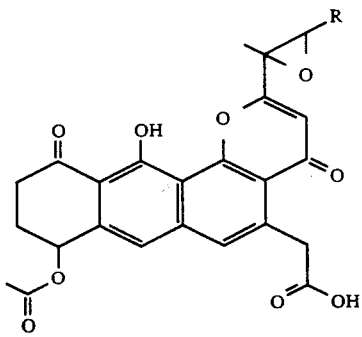

wherein R represents ethyl, propyl or 1-propenyl.

2. The compound according to claim 1, wherein said R represents ethyl.
3. The compound according to claim 1, wherein said R represents propyl.
4. The compound according to claim 1, wherein said R represents 1-propenyl.
5. A pharmaceutical composition comprising a pharmaceutically acceptable carrier and as an active ingredient, an effective amount of a compound according to claim 1.

* * * * *